United States Patent [19]

Bromander

[11] Patent Number: 5,224,933
[45] Date of Patent: Jul. 6, 1993

[54] CATHETER PURGE DEVICE

[75] Inventor: Roy C. Bromander, Salem, N.H.

[73] Assignee: C.R. Bard, Inc., Murray Hill, N.J.

[21] Appl. No.: 855,430

[22] Filed: Mar. 23, 1992

[51] Int. Cl.⁵ .......................................... A61M 29/00
[52] U.S. Cl. ................................... 604/99; 604/256
[58] Field of Search ........................... 604/95-103, 604/256; 606/192-194

[56] References Cited

U.S. PATENT DOCUMENTS

| | | |
|---|---|---|
| 2,936,761 | 5/1960 | Snyder . |
| 3,417,750 | 12/1968 | Carson . |
| 3,527,226 | 9/1970 | Hakim . |
| 3,592,184 | 7/1971 | Watkins et al. . |
| 3,726,283 | 4/1973 | Dye et al. . |
| 3,742,960 | 7/1973 | Dye et al. . |
| 3,888,249 | 6/1975 | Spencer . |
| 4,014,317 | 3/1977 | Bruno . |
| 4,323,071 | 4/1982 | Simpson et al. . |
| 4,351,341 | 9/1982 | Goldberg et al. . |
| 4,545,390 | 10/1985 | Leary . |
| 4,549,879 | 10/1985 | Groshong et al. . |
| 4,638,805 | 1/1987 | Powell . |
| 4,657,536 | 4/1987 | Dorman . |
| 4,684,363 | 8/1987 | Ari et al. . |
| 4,714,461 | 12/1987 | Gabel . |
| 4,715,378 | 12/1987 | Pope et al. . |
| 4,759,751 | 7/1988 | Gabel et al. . |
| 4,793,351 | 12/1988 | Landman et al. . |
| 4,811,737 | 3/1989 | Rydell . |
| 4,821,722 | 4/1989 | Miller et al. . |
| 4,846,174 | 7/1989 | Willard et al. . |
| 5,098,385 | 3/1992 | Walsh .................... 604/256 X |
| 5,100,385 | 3/1992 | Bromander . |
| 5,141,518 | 8/1992 | Hess et al. ................ 604/99 X |

FOREIGN PATENT DOCUMENTS

86/07249 12/1986 PCT Int'l Appl. .

OTHER PUBLICATIONS

U.S. patent application Ser. No. 07/303,647 to Roy Bromander, filed Jan. 17, 1989.

*Primary Examiner*—John D. Yasko
*Attorney, Agent, or Firm*—Morgan & Finnegan

[57] ABSTRACT

A balloon dilatation catheter device and method adapted for use in percutaneous transluminal angioplasty, where the catheter has several lumens so arranged to more efficiently channel and cleanse harmful materials from within the catheter, thereby preventing dangerous materials, such as air, from entering the body cavity where air or other gas or liquid may cause harm or death. The device includes a balloon inflation lumen for inflating/deflating a balloon on the distal end of the catheter, and a directional flow lumen having a one-way valve, which prevents flow in the reverse direction. The catheter may also include a guidewire lumen for introducing guidewires or liquids into the proximal end of the catheter for use in the distal end, which may lie within a body lumen.

9 Claims, 4 Drawing Sheets

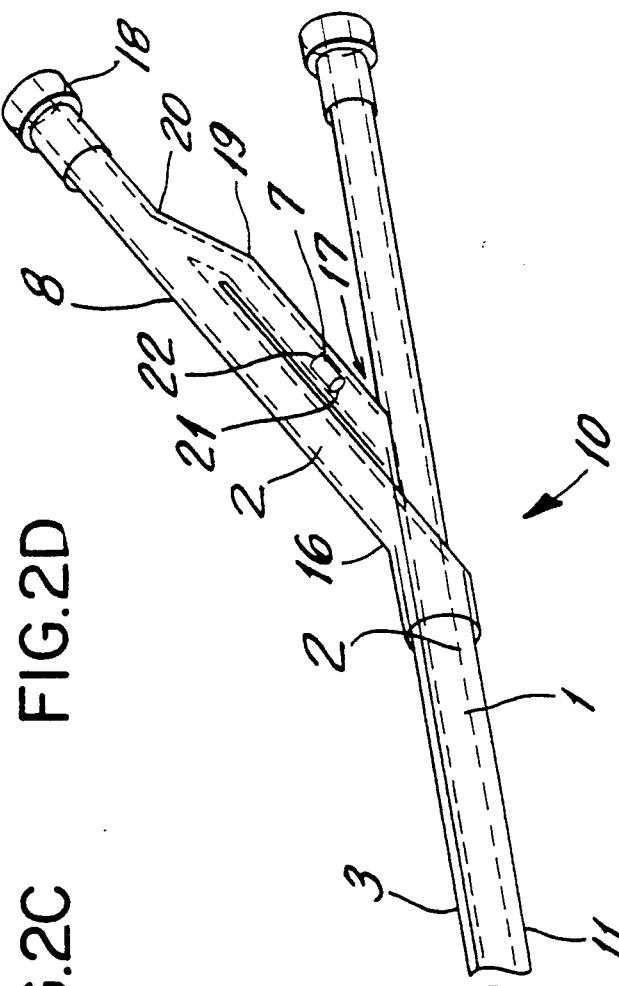
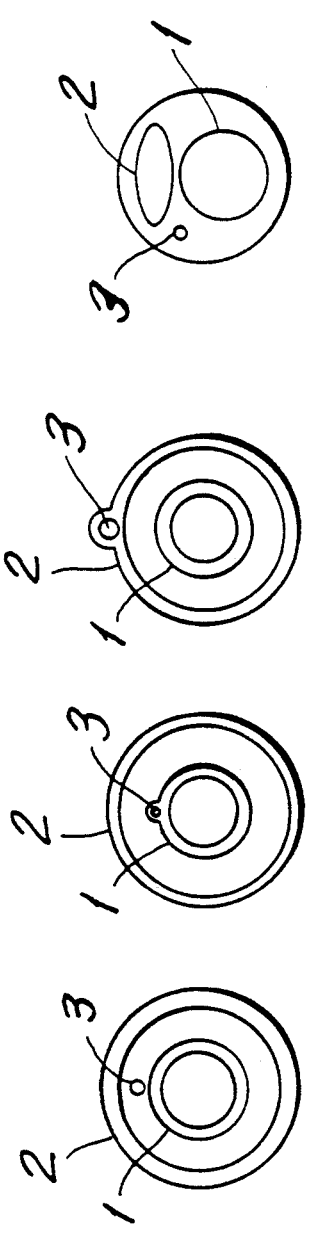
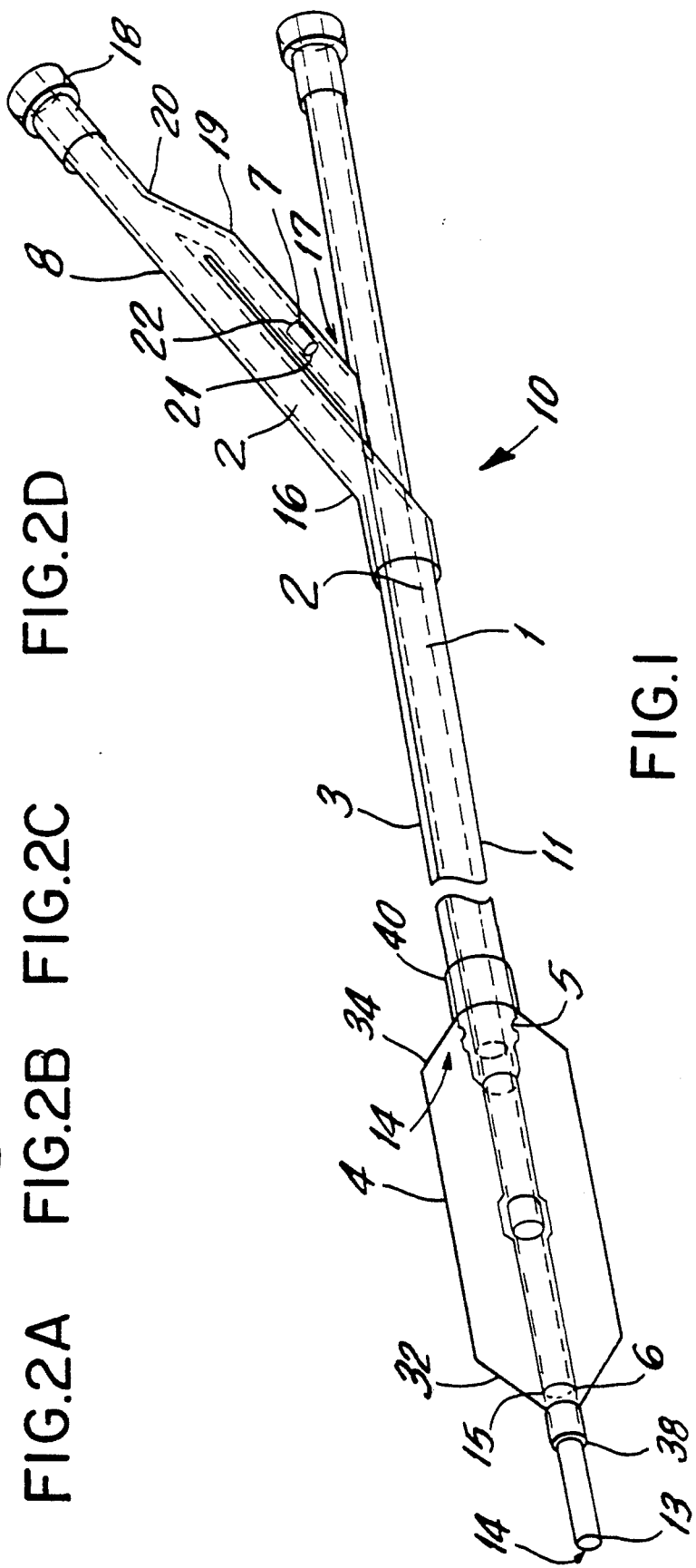

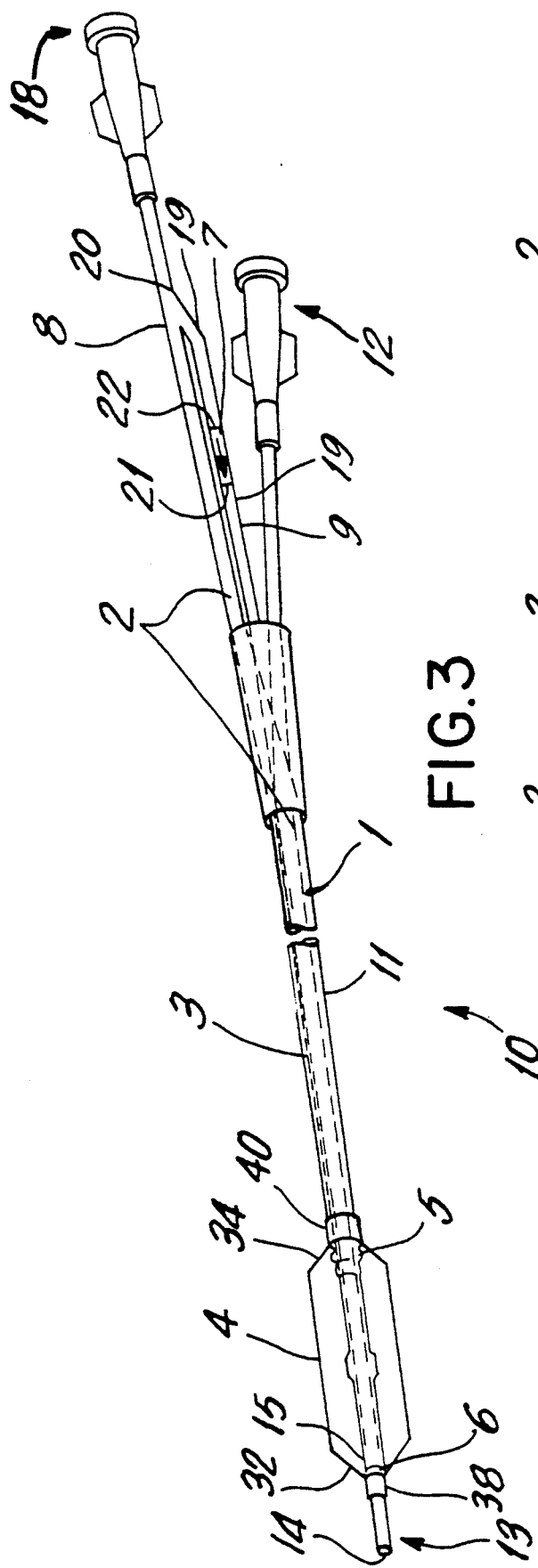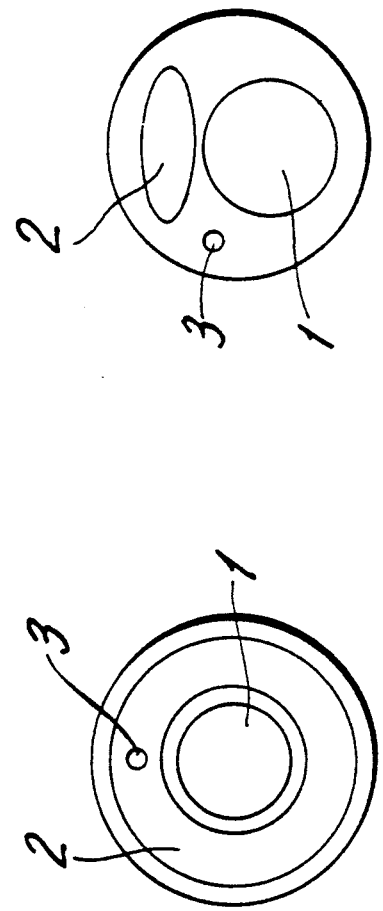

CATHETER PURGE DEVICE

BACKGROUND AND OBJECTS OF THE INVENTION

The present invention generally relates to balloon dilatation catheters, and, more particularly, to a balloon catheter having a plurality of lumens one of which contains a one-way valve permitting fluid flow in one direction and preventing fluid flow in the other direction.

Balloon dilatation catheters are used for a variety of procedures in which a body lumen or vessel is dilated. For example, such catheters are used in percutaneous transluminal angioplasty procedures in which a stenosed region of an artery, such as a coronary artery, is widened by inserting a deflated balloon into the stenosis and then inflating the balloon under pressure to forcibly enlarge the lumen through the artery. After a brief period of time, the balloon is deflated and removed. Such catheters typically have an elongate flexible shaft and a balloon mounted at the distal end of the shaft. The shaft has a balloon inflation lumen that communicates from the proximal end of the catheter to the interior of the balloon at the distal end of the shaft. The catheter also has a guidewire lumen that extends fully the length of the catheter shaft, terminating in a distal outlet at the distal tip of the shaft, beyond the balloon. The guidewire lumen may be used to receive a guidewire as well as to provide fluid communication with the interior of the patient's artery to inject radiopaque dye into the artery to visualize it fluoroscopically or to monitor the pressure in the artery, distally of the stenosis. Typically, the balloon is inflated with a liquid which is radiopaque so that the configuration and action of the balloon may be monitored fluoroscopically during the angioplasty procedure. Use of an incompressible liquid as an inflation medium assures effective development and transmission of dilating forces to the balloon and to the stenosed region of the artery that is to be dilated.

Since the balloon is used in arteries and veins, an inflation media must be selected which will avoid serious injury to the patient should the media be accidentally released into the body, e.g., upon rupture of the balloon. Because air and other gases are not quickly absorbed by the blood, they are particularly dangerous. Thus, radiopaque contrast media, either 100% or in solution with water of saline, is typically employed to fill and purge the balloon of all harmful gases. Air removal is essential not only to insure the safety of the patient but also to prevent air blocks which could limit the amount of expansion of the balloon, thereby reducing the effectiveness of the angioplasty procedure.

As a result of the foregoing dangers, various purging systems have been developed, wherein air is purged from the balloon and lumen with the subsequent insertion of radiopaque material.

One type of prior device/system is disclosed in the U.S. Pat. No. 4,323,071 to Simpson et al., which uses an arrangement where a vent tube is inserted through the balloon inflation lumen and into the balloon. When the purging liquid is introduced through the balloon inflation lumen, the air within the balloon is vented to the atmosphere from the vent tube. However, with this arrangement there is a possibility that inserting the vent tube into the flexible balloon could damage the balloon, creating leaks which may be unnoticeable. Further, this system for purging air from the catheter is somewhat time consuming and may be awkward in that it requires a number of manipulations of the vent tube. Additionally, there is some risk that the vent tube may damage the balloon. A further difficulty is that if a minute drop of liquid contacts the distal tip of the vent tube before purging is completed, the tube will become blocked by capillary action and may have to be replaced. Lastly, it may be desirable to increase the size of the lumen, requiring changing of the vent tube, which can also be a time consuming and difficult procedure.

Another type of purging device is disclosed in U.S. Pat. No. 4,545,390 to Leary, where a catheter is first evacuated by a syringe connected to the inflation lumen at the proximal end of the catheter. After air has been evacuated from the balloon, the inflation lumen and balloon are filled, by the syringe, with inflation liquid. Typically, one or more bubbles of air will remain entrapped in the balloon and, in an effort to purge as much air from the system as possible, it is the common practice to fill the balloon while holding the catheter with its distal end hanging down to permit the air to rise through the inflation lumen to the proximal end of the catheter where it may escape to atmosphere from the vented proximal end of the inflation lumen. Most, but not all of the air can be removed by this procedure. Usually, a small bubble of air will remain in the system.

Another form of purging device/method is described in U.S. Pat. No. 4,684,363 to Ari. This patent discloses a balloon dilatation catheter having a pair of parallel inflation lumens both of which extend from the proximal end of the catheter through the catheter shaft into communication with the interior of the balloon. The catheter is filled with inflation liquid by directing the liquid through one of the inflation lumens into the balloon while permitting the other lumen to vent to the atmosphere to permit air to escape. After both inflation lumens and the balloon are filled with inflation liquid, both of the lumens are connected to the inflation/deflation device and are operated in parallel to inflate or deflate the balloon. This approach requires the use of an additional lumen, which necessarily requires either that the catheter be increased in outer diameter or that the other lumens in the catheter be smaller in size, thereby diminishing their capacity. Additionally, such a three lumen catheter is more difficult to extrude, particularly in the smaller sizes of such catheters. Further, this structure and/or method is somewhat cumbersome and time-consuming, and requires a relatively high degree of skill to use successfully.

Another multi-lumen balloon catheter used for purging is described in U.S. Pat. No. 4,793,351 to Landsman et al. This patent includes a manifold having a valve connected to the proximal ends of the balloon and vent lumens and an inflation/deflation device. The valve is adapted to have several positions to permit purging of the air to the atmosphere as the catheter is filled with inflation fluid. In another position the balloon is directly connected to vent lumens, which inflate and deflate the balloon. This device requires that the valve in the manifold be manipulated from the described position.

Applicant's U.S. Ser. No. 07/303,647 discloses a Fast Purge Balloon Dilatation Catheter with a slit on the catheter shaft within the balloon, which permits fluid flow from the guidewire lumen into the balloon. The slit operates as a one-way valve and is initially covered by elastic, which opens as the pressure increases, such as where a tip occluder is inserted into the distal opening of the guidewire lumen and contrast is injected down the guidewire lumen and into the balloon. Air trapped within the balloon is then vented out the balloon lumen. Although the above catheter offers many advantages over prior catheter purging devices, the present invention describes an improved catheter purging device.

There is, therefore, a need for a purging catheter device capable of being prepared from a position outside the body for use within the body, particularly for use in percutaneous transluminal coronary angioplasty in a simple and time-saving manner that does not require excessive manipulation of parts and elements associated therewith.

It is therefore an object of this invention to provide a new or improved angioplasty catheter.

Another object of this invention is to provide a new and improved angioplasty catheter device which is constructed to reduce the time required for preparing the device for use.

A further object of this invention is to provide a new and improved angioplasty catheter device which reduces the number of manipulative steps needed to prepare the catheter for purging air from the balloon and associated lumen in preparation for use.

Another object of the invention is to provide a new and improved angioplasty catheter which can have the air removed from the balloon and associated lumens and inflation fluid provided therein in a simple manner which does not require any additional training.

A still further object of this invention is to provide a new and improved balloon catheter device which permits more complete removal of air from the balloon than has been possible heretofore.

A still further object of this invention is to provide a new and improved balloon catheter device that does not require a tip occluder which may damage the tip.

Another object of this invention is to provide a new and improved balloon catheter that does not require additional flushing of the distal lumen after purging of the balloon.

Still another object of this invention to provide a balloon catheter device wherein a prolonged vacuum can be placed in the balloon without danger of aspirating air into the system.

Another further object of this invention is to provide a new and improved balloon catheter device wherein the catheter does not vent air to the atmosphere and wherein air within said balloon is directed to an inflation/deflation device.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention includes balloon dilatation catheter devices and methods adapted for use in percutaneous transluminal angioplasty, where the catheter has several lumens so arranged to more efficiently channel and cleanse harmful materials from within the catheter, thereby preventing dangerous materials, such as air, from entering the body cavity where air or other gas or liquid may cause harm or death.

According to the preferred embodiment of the present invention, the balloon dilatation catheter device includes a guide wire lumen, a balloon inflation lumen, a directional flow lumen, and an inflatable balloon. After an initial application of vacuum to the device, any residual air within the balloon dilatation catheter device may be displaced by a pressurized injection of a non-harmful liquid, for example radiopaque liquid, through the catheter lumen system. Since the directional flow lumen has a one-way valve, however, which prevents proximal-to-distal fluid flow, the fluid moves through the balloon inflation lumen to the balloon, displacing and forcing any residual gases through the distal opening of the directional flow lumen. The displaced gases are compressed against the distal side of the one-way valve and upon application of a second vacuum, the one-way valve opens, purging the balloon catheter device of all residual air.

In an alternate embodiment, the one-way valve prevents flow in the opposite or distal-to-proximal direction. Here, the pressurized fluid injection proceeds distally through both the balloon inflation lumen and directional flow lumen, displacing and forcing any residual gases to the balloon. Upon application of a second vacuum, the one-way valve closes, leaving a reservoir of fluid within the directional flow lumen, thereby preventing the displaced air from returning and allowing simple vacuum removal of the potentially harmful air.

It will be appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part hereof, illustrate preferred embodiments of the invention and, together with the detailed description, serve to explain the principles of the invention.

BRIEF DESCRIPTION OF THE DRAWINGS

The foregoing objects and advantages of the present invention will be appreciated more fully from the following further description thereof with reference to the accompanying drawings in which:

FIG. 1 is a view of the preferred embodiment of the balloon dilatation catheter device of the present invention where the balloon is in an inflated condition;

FIGS. 2A-2D are alternate cross-sectional views of various configurations of the lumens of the balloon dilatation catheter device shown in FIG. 1;

FIG. 3 is a view of an alternative embodiment of the balloon dilatation catheter device of the present invention with the balloon inflated;

FIGS. 4A-4D are cross-sectional views of two configurations of the lumens of the balloon dilatation catheter device shown in FIG. 3;

DETAILED DESCRIPTION OF PREFERRED EMBODIMENTS

Figure 5:
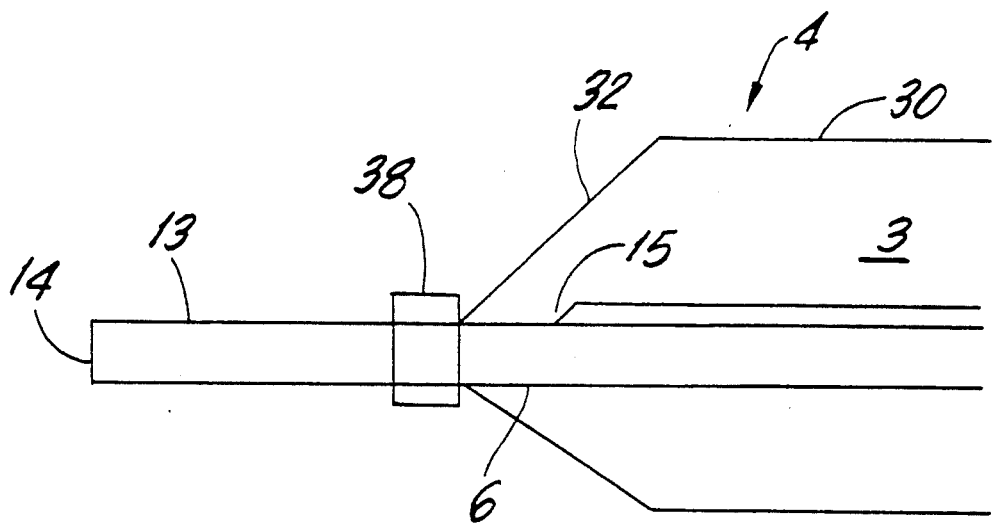
FIG. 5 is an enlarged, broken-away illustration of the balloon on the distal end of the balloon catheter devices shown in FIGS. 1 and 3.
Figure 6B:
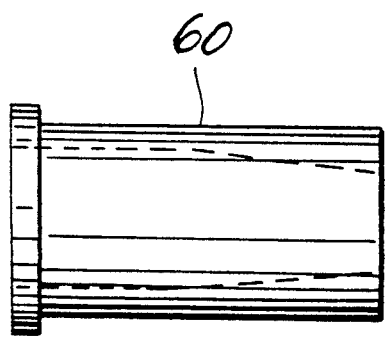
FIG. 6B is a top view of the one-way valve shown in FIG. 6A illustrating in outline the tapering of the inner diameter.
Figure 6A:
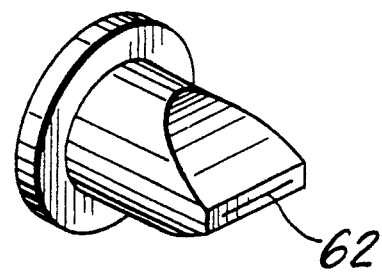
FIG. 6A is a perspective view of a preferred one-way valve used in the present application.
Figure 6C:
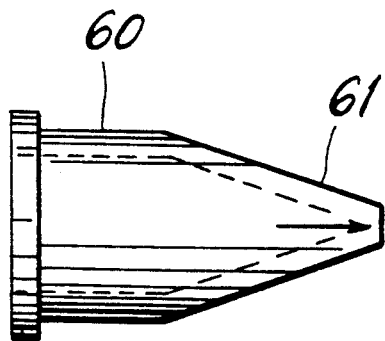
FIG. 6C is a side view of the one-way valve shown in FIG. 6A also showing the tapering of the inner diameter.
Figure 6D:
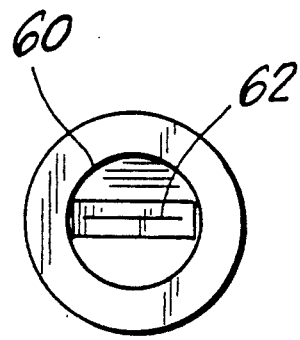
FIG. 6D is a front end view of the one-way valve shown in FIG. 6A.
Figure 4C:
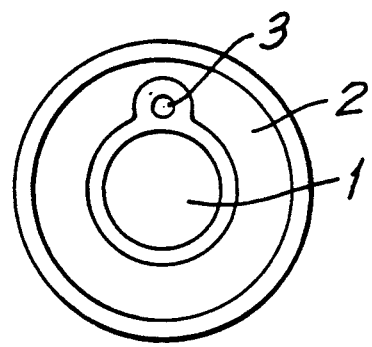
Figure 4D:
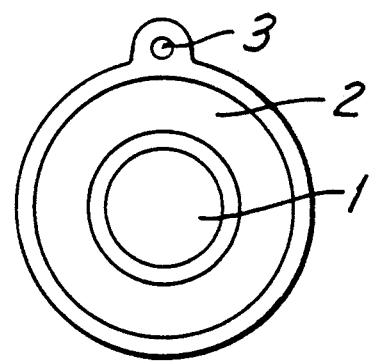

Referring now to the accompanying drawings, wherein like reference characters refer to like parts throughout the various views, there are shown in FIGS. 1-4 the preferred embodiments of the Balloon Dilatation Catheter device according to the present invention.

Referring first to FIG. 1, there is shown a preferred embodiment of the present invention (indicated generally at 10) adapted for use in balloon dilatation. As here embodied, balloon dilatation catheter device 10 comprises a catheter shaft 11, guide wire lumen 1, a balloon inflation lumen 2, a directional flow lumen 3, and a balloon 4, all integrated into a unitary assembly as more fully described below.

The balloon dilatation catheter device of the present invention includes an elongate flexible catheter 11 that may be formed, as by extrusion, from an appropriate plastic material such as polyvinyl chloride, polyethylene or the like. By way of example, a balloon dilatation catheter suitable for percutaneous transluminal coronary angioplasty may be of the order of 150 cm long and of the order of 0.45" outer diameter and 0.039" inside diameter. Catheter 11 preferably has a proximal end portion 12 and a distal end portion 13, both of which are open. The distal end portion 13 of catheter 11 is the portion inserted and navigated through a body lumen, such as an artery or vein to a desired location, for example, an area with stenosis. The tip 14 of distal catheter end portion 13 must be relatively smooth to safely navigate arteries or veins narrowed by plaque without puncturing the artery/vein wall or loosening plaque from the vessel walls.

A guide wire lumen 1 extends axially along the length of catheter 11 and is open at the proximal end portion 12, into which a guide wire or other device may be externally inserted, and open at the distal end portion 13, from which the inserted guide wire or device may be maneuvered internally. The guide wire lumen may also be used to introduce fluid into the interior of the patient's artery or vein, for example, injecting a radiopaque dye in order to visualize the body lumen fluoroscopically. FIGS. 2A-2D show various positional locations of the guide wire lumen 1 within catheter 11. Guide wire lumen 1 preferably has an inside diameter of about 0.019" and an outer diameter of about 0.030". As shown in FIG. 1, guidewire lumen 1 extends axially from the open proximal end portion 12 to distal end portion 13 of catheter 11.

As shown in FIGS. 2A-2D, catheter 11 is also formed with a balloon inflation lumen 2. As preferably embodied, a connection is formed at the proximal end of catheter 11. Although balloon inflation lumen 2 extends axially along most of the length of catheter 11, balloon inflation lumen 2 preferably separates from catheter shaft 11 at a junction point 16 near the proximal end portion 12, and preferably continues at an angle through a balloon inflation leg 8 connected to catheter 11 at juncture point 16. The balloon inflation lumen 2 is open at a proximal end portion 18 of the balloon inflation leg 8, wherein liquids or gasses may be injected or withdrawn under pressure or vacuum.

A dilation balloon 4 is attached at the distal end portion 13 of catheter 11. Said balloon may be formed from a polymeric material adapted to be formed into a thin wall, highly flexible and relatively inelastic balloon. The balloon may be formed as described in U.S. Pat. No. 4,490,421 to Levy. The balloon 4 includes a central cylindrical section 30 and a pair of end cones 32 and 34 and mounting collars 38 and 40 by which the balloon 4 is mounted to the catheter shaft 11, forming an air-tight seal. Balloon inflation lumen 2 terminates within balloon 4 at a balloon inflation lumen opening 14, preferably near the proximal cone portion 5, located distally of proximal mounting collar 40, and within balloon 4.

A third lumen, a directional flow lumen 3, is also shown in FIG. 1 and in cross-section in FIGS. 2A-2D. Directional flow lumen 3 has a substantially smaller diameter than the other lumens and runs parallel with guide wire lumen 1 and balloon inflation lumen 2 through much of catheter 11. Directional flow lumen 3 preferably has an inside diameter of 0.03", and as preferably embodied, is fabricated separately from guide wire lumen 1 and balloon inflation lumen 2, as shown in FIG. 2A, forming three separate lumens and requiring three extrusions. In FIGS. 2B and 2C, two extrusions are required, and in FIG. 2, a single extrusion forms the three lumens. In the preferred embodiment of FIG. 1, directional flow lumen 3 terminates slightly distal to the balloon inflation lumen opening 14. Directional flow lumen 3 is extended by coaxial extension tube 45 effectively creating a directional flow lumen opening 15, preferably near distal end cone portion 6, located proximally of distal mounting collar 38, and within balloon 4, as shown in FIG. 5. Directional flow lumen 3 thus extends proximally along catheter 11 parallel with guidewire lumen 1 and balloon inflation lumen 2. Directional flow lumen 3, however, terminates prior to reaching the proximal end portion 12 of catheter 11, and communicates with balloon inflation lumen 2 through a one-way valve 7, which may be positioned within said directional flow lumen 3.

As noted, in the preferred embodiment, balloon inflation lumen 2 splits off from catheter 11 and guidewire lumen 1, and instead extends through balloon inflation leg 8, which in turn may have a side branch lumen 19 which connects the balloon inflation lumen 2 with directional flow lumen 3 at a juncture point 17. Between the point of departure of side branch lumen 19 from the balloon inflation leg 8 (indicated generally at departure point 20) and juncture point 17, side branch lumen 19 has a one-way valve 7, which only allows flow in a distal-proximal direction, i.e., in a direction from juncture 17 up side branch lumen 19 towards the proximal end portion 18 of balloon inflation leg 8. Examples of preferred one-way valves 7 include a duckbill valve as manufactured by Vernay Laboratories, as shown in FIG. 6, and a valve having a filter membrane as manufactured by Porex Technologies, not shown, which allow gases such as air to pass through, but which prevents fluids, such as contrast media, from passing through.

As shown in FIG. 6, a preferred one-way valve 7 includes a substantially cylindrical tube 60, which tapers at one end 61 to form a narrow slit 62. Fluids, for example contrast media, readily flow through narrow slit 62 from tube 60 out through slit 62, but do not so readily flow in the reverse direction from outside narrow slit 62 into slit 62. Thus, positioning the preferred one-way valve 7 so that the end 61 of one-way valve 7 forms the proximal end 22, creates the desired distal-to-proximal fluid flow in this embodiment of the present invention.

Normal operation of the fully assembled balloon dilatation catheter device includes connecting the balloon inflation leg 8 to an external inflation/deflation device (not shown). Application of a vacuum results in the evacuation of air from the balloon inflation lumen 2, balloon 4, and directional flow lumen 3. Upon removal of the vacuum, contrast material is then injected under pressure into the balloon inflation lumen 2 of balloon inflation leg 8. Since one-way valve 7 prevents fluid flow through side branch lumen 19, the contrast media does not initially flow through directional flow lumen 3. Instead, the contrast media flows through balloon inflation lumen 2, and eventually reaches balloon 4, and begins to fill the balloon through the distal opening 14 of said balloon inflation lumen 2 at the proximal cone portion 5 of balloon 4. Any remaining air or other gas within balloon 4 is pushed distally to the distal cone portion 6 of the balloon 4. Preferably, during the purging of balloon 4, the distal end of catheter 11 is held upwards, whereby the air within balloon 4 is forced into the opening 15 of the directional flow lumen 3, and along the directional flow lumen 3 to the now "closed" one-way valve 7, i.e. the fluid on the proximal end 22 of the one-way valve 7 forms a barrier. The displaced air within directional flow lumen 3 is thus compressed against the distal side 21 of one-way valve 7, which continues to resist the flow of contrast through narrow slit 62 on the proximal side 22 of one-way valve 7. Although the external inflation/deflation device still applies pressure on the proximal end 22 of one-way valve 7, the valve remains "closed" despite the pressure of the displaced gas against the distal end 21 of one-way valve 7. The injection of contrast media preferably continues until the injection pressure exceeds a predetermined amount, preferably under 20 atmospheres. Most preferably, contrast media is injected at a pressure of approximately 5 atmospheres.

Application of a second vacuum at the proximal end portion 18 of the balloon inflation leg 8 "opens" one-way valve 7, releasing the displaced air or gas on the proximal end 22 to the inflation/deflation device. Since all the displaced air within the various catheter lumens is compressed against the distal portion 21 of one-way valve 7 and also pushed by a reservoir of fluid behind the gas in directional flow lumen 3, the present invention has removed all gases from the balloon dilatation catheter device 10, providing a simpler and thorough prepping of catheter 11.

Catheter 11 is now purged of any potentially harmful gases, which, if released within the blood stream or other body lumen, could cause serious injury or death.

Referring now to FIGS. 3 and 4A-4D, there is shown an alternative embodiment of the balloon dilatation catheter 11 of the present invention. Because the catheter shown in FIG. 3 includes some of the same elements illustrated in FIG. 1, hereinbefore described in detail, identical reference numbers will be used for many of these elements and a detailed description of this physical characteristic and operations will be omitted.

As preferably embodied, balloon dilatation catheter device 10 comprises a guide wire lumen 1, balloon inflation lumen 2 having a side branch 19 connected to a directional flow lumen 3, and a balloon 4, all integrated into a unitary assembly as shown in FIG. 3 and as more fully described above with respect to the preferred embodiment shown in FIG. 1.

The device shown in FIG. 3 differs from that in FIG. 1, however, by the direction of flow in one-way valve 7. The valve 7 in this embodiment allows flow in a proximal-distal direction, i.e., in a direction from the external inflation/deflation device connected at the proximal end portion 18 of balloon inflation leg 8 down side branch lumen 19 towards juncture 17 and into the directional flow lumen 3. Consequently, end 61 with slit 62 forms the distal end 21 of one-way valve 7, creating the desired proximal-to-distal fluid flow in this embodiment.

Operation of the balloon catheter device 10 shown in FIG. 3 is initiated by attaching balloon inflation leg 8 to an external inflation/deflation device (not shown) filled with contrast media. Application of a first vacuum results in the evacuation of air from the balloon inflation lumen 2, balloon 4 and directional flow lumen 3. Contrast material is then injected under pressure into balloon inflation lumen 2 of balloon inflation leg 8. The contrast material flows through balloon inflation lumen 2 and into side branch lumen 19. Since one-way valve 7 is "open," it allows media to travel down the directional flow lumen 3. The contrast media then moves through both the balloon inflation lumen 2 and directional flow lumen 3 towards balloon 4, displacing any gases present. Any remaining air or other gas within the balloon inflation lumen 2 or directional flow lumen 3 is preferably compressed toward and within balloon 4.

Application of a second vacuum at the proximal end portion 18 of balloon inflation leg 8 pulls the contrast media in balloon inflation lumen 2 and the remaining displaced air out of the balloon 4 through the balloon inflation lumen 2 and into the external inflation/deflation device.

Since one-way valve 7 operates in a proximal-distal direction, the valve prevents fluid flow through slit 62 during the second vacuuming process, thus, the fluid in balloon inflation lumen 2 is withdrawn first, and then the fluid and displaced air in balloon 4. The reservoir of fluid within the axial length of the directional flow lumen 3 is then withdrawn by the vacuum through the balloon 4 and balloon inflation lumen 2, pushing any residual air towards the vacuum. The reservoir of fluid within the directional flow lumen 3 insures that all the remaining displaced air within balloon 4 is withdrawn by the second vacuum, completing the prepping of catheter 11.

Catheter 11 is now purged of any potentially harmful gases, which, if released within the body, could cause serious injury or death.

It will be understood by those skilled in the art that the present invention in its broader aspects is not limited to the particular embodiments shown and described herein, and that variations may be made which are within the scope of the accompanying claims without departing from the principles of the invention and without sacrificing its chief advantages.

I claim:

1. A catheter device for deflating and inflating a balloon positioned on a distal end of said catheter, comprising:
    (a) a catheter having a flexible deflatable/inflatable balloon in its distal region and adapted to have a deflation/inflation device connected to its proximal end;

(b) a balloon inflation lumen communicating with said balloon at the proximal end of said balloon and extending axially along the catheter and adapted to communicate with a deflation/inflation device at its proximal end;

(c) a directional flow lumen having a substantially smaller diameter than said balloon inflation lumen and distally terminating at the distal end of said balloon, said directional flow lumen extending axially along the length of the catheter and communicating with said balloon inflation lumen at the proximal end of said balloon inflation lumen, and distally of the proximal end of said balloon catheter; and (d) one-way valve means positioned within the directional flow lumen at the proximal region of said catheter and distally of the proximal end thereof.

2. The catheter device according to claim 1, wherein said one-way valve permits flow within said directional flow lumen in a distal to proximal direction within said directional flow lumen, and wherein said one-way valve prevents flow in said directional flow lumen in a proximal to distal direction.

3. The catheter device according to claim 1, wherein said one-way valve permits flow within said directional flow lumen in a proximal to distal direction within said directional flow lumen, and wherein said one-way valve prevents flow in said directional flow lumen in a distal to proximal direction.

4. The catheter device according to claim 1 further comprising a guidewire lumen extending axially along said catheter.

5. The catheter device according to claim 1, wherein said one-way valve is positioned within a side branch of said balloon inflation lumen at the proximal end of said catheter, where the distal end of said one-way valve communicates with said directional flow lumen and the proximal end of said one-way valve communicates with said balloon inflation lumen.

6. A catheter device according to claim 1, wherein said one-way valve means is constructed and arranged to prevent reverse flow through said one-way valve up to pressures of about 20 atmospheres.

7. A method for purging gases from catheter system, comprising the following steps:

(a) applying a first vacuum on the proximal end portion of a balloon inflation lumen within said catheter, wherein said vacuum withdraws air from said balloon inflation lumen, balloon, and a directional flow lumen;

(b) injecting a harmless fluid within said balloon inflation lumen, said fluid displacing any residual air remaining after said first vacuum step and forcing said residual air to a single, accessible location; and (c) applying a second vacuum on said balloon inflation lumen, wherein said residual air is readily removed from said accessible location.

8. The method according to claim 7, wherein a one-way valve means remains closed during said injection step, wherein said residual air is displaced to the distal end of a one-way valve within said directional flow lumen, and wherein said second vacuum step opens said one-way valve means, releasing said residual air on the distal end of said one-way valve.

9. The method according to claim 7, wherein a one-way valve means remains open during said injection step, wherein said residual air is displaced to said balloon on the distal end of said catheter, wherein said injected fluid fills said balloon inflation and directional flow lumens, and wherein said second vacuum step closes said one-way valve means, leaving a reservoir of fluid within said directional flow lumen.

* * * * *